US009362081B2

(12) United States Patent
Bleuet et al.

(10) Patent No.: US 9,362,081 B2
(45) Date of Patent: Jun. 7, 2016

(54) SOURCE OF X-RAYS GENERATING A BEAM OF NANOMETRIC SIZE AND IMAGING DEVICE COMPRISING AT LEAST ONE SUCH SOURCE

(71) Applicant: COMMISSARIAT A L'ENERGIE ATOMIQUE ET AUX ENE ALT, Paris (FR)

(72) Inventors: Pierre Bleuet, Seyssins (FR); Nicolas Martin, Peyrieu (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 247 days.

(21) Appl. No.: 14/021,367

(22) Filed: Sep. 9, 2013

(65) Prior Publication Data
US 2014/0072102 A1 Mar. 13, 2014

(30) Foreign Application Priority Data
Sep. 10, 2012 (FR) .................................... 12 58446

(51) Int. Cl.
*H01J 35/08* (2006.01)
*H01J 35/04* (2006.01)
*G21K 7/00* (2006.01)
*G01N 23/04* (2006.01)

(52) U.S. Cl.
CPC ............... *H01J 35/04* (2013.01); *G01N 23/04* (2013.01); *G21K 7/00* (2013.01); *H01J 35/08* (2013.01)

(58) Field of Classification Search
CPC ....... H01J 35/04; H01J 35/08; H01J 2235/08; H01J 2235/081; H01J 2235/086; H01J 2235/088
See application file for complete search history.

(56) References Cited

U.S. PATENT DOCUMENTS

| 7,130,375 | B1 | 10/2006 | Yun et al. | |
| 2004/0240613 | A1* | 12/2004 | Hamann et al. | ............... 378/119 |
| 2006/0133576 | A1* | 6/2006 | Wilkins | .................. H01J 35/08 378/124 |
| 2012/0082396 | A1 | 4/2012 | Crandall et al. | |
| 2013/0028380 | A1 | 1/2013 | Bleuet et al. | |
| 2013/0032713 | A1* | 2/2013 | Barbi et al. | ................... 250/307 |

FOREIGN PATENT DOCUMENTS

WO 01/99478 A1 12/2001
WO WO 2004/064168 7/2004

OTHER PUBLICATIONS

L.A Giannuzzi, et al., "A Review of Focused Ion Beam Milling Techniques for TEM Specimen Preparation", Micron, vol. 30, 1999, pp. 197-204.
Bart Pauwels, et al., "X-ray Nanotomography in a SEM", Proc. SPIE 7804, 78040S, 2010, 8 Pages.

(Continued)

*Primary Examiner* — David J Makiya
*Assistant Examiner* — Dani Fox
(74) *Attorney, Agent, or Firm* — Oblon, McClelland, Maier & Neustadt, L.L.P.

(57) ABSTRACT

A source of X-rays, and imaging device, and an imaging process are provided, including a source of electrons generating an electron beam of nanometric size and a target, the target being designed to send out an X-ray beam upon illumination by the electron beam, the target including one nanowire, for example made of silicon, and a nanowire catalyst, for example made of gold, covering the free end of the nanowire.

20 Claims, 9 Drawing Sheets (56) References Cited

OTHER PUBLICATIONS

Yewu Wang, et al., "Epitaxial Growth of Silicon Nanowires Using an Aluminium Catalyst", Nature Nanotechnology, vol. 1, Dec. 2006, pp. 186-189.

Lucille A. Giannuzzi, et al., "FIB Lift-Out Specimen Preparation Techniques. An Introduction to Focused Ion Beams", Springer US, 2005, pp. 200-228 (with Cover Page and Table of Contents).

Hua Wang, et al., "A Top-Down Approach to Fabrication of High Quality Vertical Heterostructure Nanowire Arrays", Nano Letters, vol. 11, No. 4, 2011, pp. 1646-1650.

Barbara Zitova, et al., "Image Registration Methods: a Survey", Image and Vision Computing, vol. 21, 2003, pp. 977-1000.

Erik Meijering, "A Chronology of Interpolation: From Ancient Astronomy to Modern Signal and Image Processing", Proceedings of the IEEE, vol. 90, No. 3, Mar. 2002, pp. 319-342.

Alan Conrad Bovik, "The Essential Guide to Image Processing", Elsevier, 2009, p. 110 (Chapter 5, Paragraph 5.4.6).

French Preliminary Search Report issued Jul. 11, 2013, in Patent Application No. FR 1258446, filed Sep. 10, 2012 (With English Translation of Category of Cited Documents).

\* cited by examiner

SOURCE OF X-RAYS GENERATING A BEAM OF NANOMETRIC SIZE AND IMAGING DEVICE COMPRISING AT LEAST ONE SUCH SOURCE

TECHNICAL FIELD AND PRIOR ART

The present invention relates to a source of X-rays generating an X-ray beam of nanometric size and an imaging device comprising at least one such source, said device being particularly adapted to the characterisation of embedded nanometric structures, and even more particularly adapted to the characterisation of three-dimensional embedded nanometric structures.

The rise of microelectronics and of 3D nanoelectronics, that is, the three-dimensional integration of microsystems and nanosystems involves utilising means of observation of nanometric structures embedded at several hundreds of micrometers in the material.

Also, microstructures and nanostructures generally have a three-dimensional structure to be displayed in high resolution, down to a nanometer, by three-dimensional characterisation techniques resolved spatially and in depth.

Now, conventional methods based on optical microscopy, electron microscopy, or ion beams do not allow such observation as interactions involved allow only to see the surface of the specimens.

To observe embedded systems, the most penetrating X-rays are used to probe the material in depth by exploiting the attenuation difference of X-rays by the different materials.

Conventional X-ray and tomography X techniques are classically applied to materials, on a scale ranging from a millimeter to a micrometer. These techniques use an X-ray tube which illuminates the specimen, and the reflected rays are collected by a detector. These techniques offer sufficient efficacy for these scales.

However, to achieve higher resolutions, that is, clearly less than a micrometer, the X-ray tubes are no longer adapted.

In fact, current X-ray tubes are limited by heating of the cathode and by electron-cathode interaction which is at the origin of X-ray sources of excessive sizes and therefore incompatible with the preferred nanometric resolutions.

To generate a beam of rays of the order of a nanometer, a Scanning Electron Microscope (SEM) can be used whereof the optics conventionally create beams of electrons whereof the size is of the order of a nanometer.

This electron beam interacts with a target which in turn generates an X-ray beam, at the same time by braking radiation (continuous spectrum) and by fluorescence radiation. The composition and the geometric arrangement of the target, as well as the energy of the electrons determine the distribution of energy, or spectrum, of the resulting X-ray beam.

This technique has a major disadvantage. In fact the electron-target interaction is described by an <<interaction volume>> whereof the characteristic size can reach several hundreds of nanometers, even in the case where the incident beam measures a few nanometers only. The source of X-rays formed in this way has a size of several hundreds of nanometers, which is greater than the preferred size of X-ray beam. Such a beam diameter fails to produce sufficient resolution.

EXPLANATION OF THE INVENTION

It is consequently an aim of the present invention to provide a source of X-rays generating an X-ray beam of nanometric size adapted to the nanostructure observation.

It is also an aim of the present invention to provide an imaging device adapted to observation of embedded microstructures and nanostructures with good resolution.

These aims are attained by a source of X-rays providing a beam whereof the diameter is of a nanometric order comprising a source of electrons whereof the beam is of nanometric diameter and a target for generation of X-rays, the target being formed by at least one nanostructure comprising at a free end material capable of generating high-energy X-rays.

In an advantageous example, the nanostructure is formed by a nanowire bearing at its free end the nanowire catalyst, of material of high atomic number, for example made of gold or copper, used previously for forming the nanowire. The size of this nanowire catalyst is generally between 10 nm and 50 nm and mainly defines the diameter of the interaction volume. The result is that the X-ray beam has a diameter of 10 nm and 50 nm.

Thanks to the invention, the X-rays source is limited to the area of the nanowire which is in materials with high atomic number, i.e., the catalyst. The width of the interaction volume is then limited to the width of the catalyst. on the contrary, in the device of state of the art the interaction between the electron beam and the tip happens in a wide area, the interaction volume is then bigger that the interaction volume of the invention. The X-rays source is then bigger and the resolution is lower.

As a variant, the nanostructure can even be made by etching or by ionic machining of a silicon substrate covered by a layer of material capable of generating high-energy X-rays, for example made of gold, copper or tungsten.

In another particularly advantageous example, a plurality of nanostructures is used, each nanostructure being successively lit by the electron beam, which reduces the heating of each of the nanostructures. Adapted processing of the data supplied by each of the nanostructures compensates the variation in position of each of the nanostructures relative to the specimen and averages the images to create a single virtual image.

The source of electrons is advantageously formed by a scanning electron microscope.

The device comprises a source of X-rays according to the invention, a specimen holder and a detector. The detector can be based on direct or indirect detection. Also, the specimen holder is preferably mobile, and it preferably has six degrees of liberty. Rotation of the specimen holder allows observation by tomography of the specimen.

The subject-matter of the present invention is a source of X-rays comprising a source of electrons generating an electron beam of nanometric size and a target, said target being designed to emit an X-ray beam by illumination by the electron beam, said target comprising at least one nanostructure, said nanostructure comprising a first portion of material capable of generating low-energy X-rays and a second portion of material capable of generating high-energy X-rays, the first portion being attached to a substrate by an end and the second portion covering a free end of the first portion, said first and second portions having a diameter between 1 nm and 100 nm.

Preferably, the material of the first portion has an atomic number less than 15, for example this can be silicon or carbon.

Preferably also, the material of the second portion has an atomic number greater than 20, for example this can be gold or copper.

Advantageously, the materials of first and second portions offer good thermal conductivity.

In a particularly advantageous embodiment, the target comprises a plurality of juxtaposed nanostructures. The distance separating two adjacent nanostructures can be of the order of some tens of nanometers.

The source of electrons is preferably a scanning electron microscope, the latter being particularly adapted in the case of a target having several nanostructures.

The disposition of the nanostructures can be registered in a scanning control of the scanning electron microscope so that the electron beam sent by the scanning electron microscope successively illuminates all the nanostructures.

Preferably, the height of the nanostructure is greater than or equal to 500 nm.

In an advantageous embodiment, the first portion is formed by a nanowire and the second portion is formed by a catalyst having served to form the nanowire.

In another embodiment, the nanostructure is made by etching, for example reactive ionic etching, in a substrate formed in the material of the second portion covered by a layer in the material of the first portion.

In another, the nanostructure is made by machining, for example by ionic machining, in a substrate formed in the material of the second portion covered by a layer in the material of the first portion.

Another subject-matter of the present invention is an imaging device by X-rays comprising at least one source according to the invention, a specimen holder designed to hold the specimen and at least one direct or indirect detector of rays transmitted by the specimen.

Preferably, the specimen holder is mobile at least in rotation so as to allow imagery by tomography.

The detector can be a photon-counting X-ray detector.

Another subject-matter of the present invention is an imaging process of a specimen comprising at least one microstructure and/or at least one nanostructure using the device according to the invention, comprising the steps of:

a) illumination of the nanostructure by the electron beam, b) collection by the detector of X-rays transmitted by the specimen so as to obtain a radiograph of the specimen.

Advantageously, the source of radiographs comprises several juxtaposed nanostructures and the source of electrons is a scanning electron microscope, in which steps a) and b) are applied successively to each nanostructure, said process comprising the additional steps of:

c) processing of each of the radiograph so as to produce radiograph s providing the same enlargement and/or being readjusted relative to a reference radiograph, d) averaging of the X-rays processed in this way.

BRIEF DESCRIPTION OF THE DRAWINGS

The present invention will be more clearly understood from the following description and the attached diagrams, in which.

DETAILED EXPLANATION OF PARTICULAR EMBODIMENTS

Figure 1:
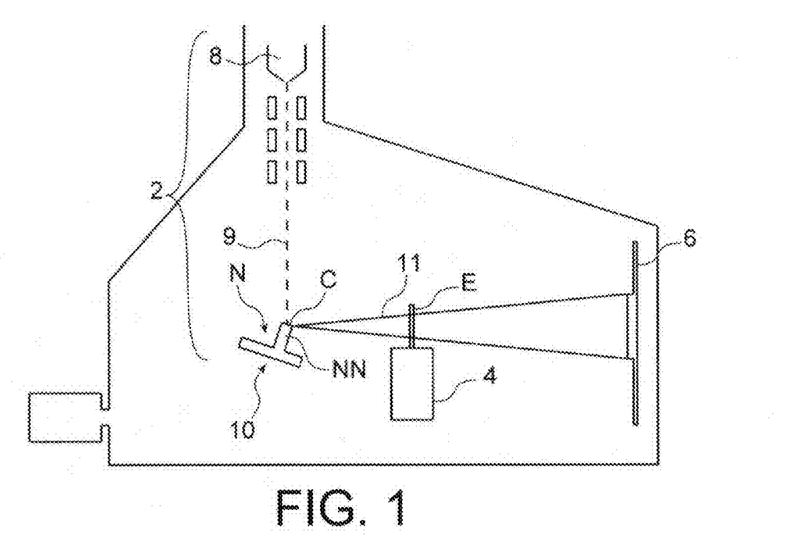
FIG. 1 is a schematic illustration of an embodiment of an X-ray imaging device according to the present invention.

FIG. 1 shows a schematic illustration of an X-ray imaging device for microstructures and nanostructures comprising a source of X-rays 2, a specimen holder 4 and a detector of X-rays 6.

The source of X-rays 2 comprises a source of electrons 8 and a target 10 generating an X-ray beam 11 under the effect of the electron beam. The source of electrons 8 can be formed by any electron canon capable of delivering a sufficiently intense and sufficiently fine beam 9 to limit losses. It can be an electron canon fitted with electronic lenses.

Advantageously, the source of electrons 8 is formed by a scanning electron microscope, designated hereinbelow "SEM". As will be evident hereinbelow the scanning of the beam is particularly interesting in an embodiment of the present invention. The structure and the operation of the SEM are well known to the man skilled in the art and will not be described in detail. As is known, the optics of the SEM create beams of electrons whereof the size is of the order of a nanometer. This electron beam interacts with the target which in turn generates X-rays, at the same time by braking radiation (continuous spectrum) and by fluorescence radiation.

The specimen holder 4 is designed to hold the specimen E to be imaged, and which will be illuminated by the X-ray beam sent by the target 10. Advantageously, the specimen holder 4 has six degrees of liberty, that is, it is mobile along three axes and about these three axes. Rotating of the specimen allows observation by tomography.

The X-ray detector 6 can be of direct detection or indirect detection type.

In the case of a direct detection detector, the X-ray cone geometrically enlarges the object on the detector.

In the case of an indirect detection detector, the geometric enlargement of the object can be coupled to optical enlargement: the X-rays transmitted by the object from the nano-source interact with a scintillation screen the role of which is to convert this radiation into visible radiation.

The visible image is enlarged by optics and the image enlarged at the same time by X-ray enlargement and by the visible enlargement is registered on a conventional CCD camera. This type of indirect detection is also known and will not be described in detail.

According to a first embodiment formed the target is by a nanostructure N comprising a nanowire NN and a nanowire catalyst C located at the free end of the nanowire NN.

In the present application, "nanostructure" means a structure of diameter, and more generally of transversal dimension, between 1 nm and 100 nm.

For the sake of simplicity, the nanowire catalyst will be designated solely by "catalyst" throughout the description.

Figure 2:
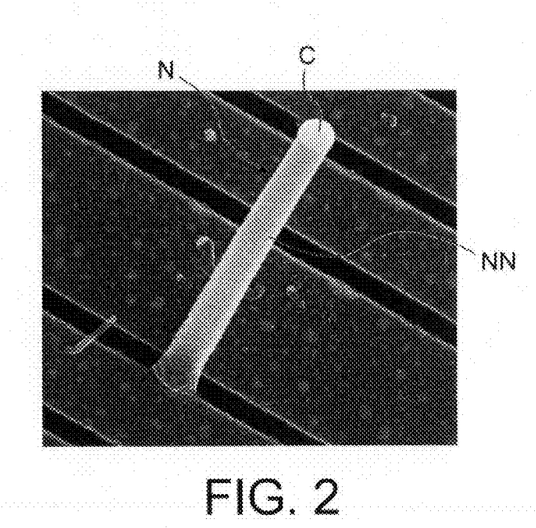
FIG. 2 is a detailed view of an example of a target which can be used in the source of FIG. 1.

FIG. 2 shows an example of a nanostructure formed by a catalyst C located at the end of a nanowire NN, the whole forming the target for generation of X-rays.

The catalyst C is conventionally used to produce nanowires and generally plays no further role.

In the device according to the invention, it plays the role of target for generating high-energy X-rays.

As is known, a fine layer of catalyst, gold for example, is deposited on a substrate, for example made of silicon and then an annealing operation is conducted under vacuum, which forms gold-silicon particles. By introducing a gaseous silicon precursor at a temperature greater than the eutectic, the resulting particles grow in certain directions and form nanowires of silicon; at the apex of this nanowire is the catalyst, made of gold, with the typical size reaching 10-50 nm. This method for growing nanowires is the <<bottom-up>> method and is described for example in the document Wang, Y et al, *Nature Nanotechnology* 1, pp 186-189, 2006.

On the one hand gold is capable of generating high-energy X-rays and on the other hand silicon contributes little to generating X-rays, mainly generating low-energy rays which contribute very little to the signal on the detector.

The catalyst is the majority source of X-rays. The transversal dimensions of the interaction volume are limited by the transversal dimension of the catalyst, since there is no material around the catalyst in a transversal direction which can generate X-rays. In the example shown, the transversal cross-section is a disc, the diameter of the catalyst delimiting the interaction volume of the X-rays; as the diameter of the catalyst is for example of the order of 10 nm, this produces a source of X-rays of nanometric size.

Figure 3:
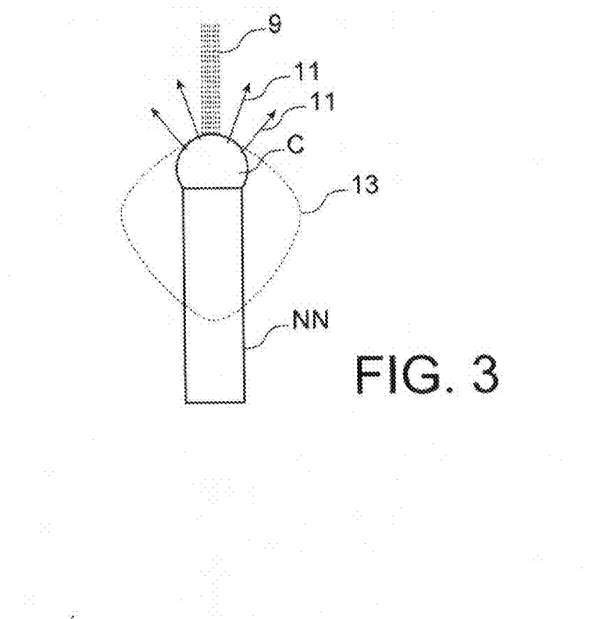
FIG. 3 is a schematic illustration of the interaction volume of the target for generation of X-rays of FIG. 2.

FIG. 3 shows a schematic illustration of a source of X-rays formed by a nanowire and the nanowire catalyst carried at the free end of the nanowire, and of the interaction volume 12 which is hatched and is in fact formed by the catalyst C and part of the nanowire NN. In the case of a wide target known from the prior art the interaction volume 13 is shown in dots. Substantial reduction of the latter is noted.

Preferably, the typical diameter of a nanowire and therefore of the catalyst for creating a source of X-rays of nanometric size is between 10 nm and 100 nm, so as to create enough signal while restricting the interaction volume.

The height of the nanostructure is selected greater than the size of the interaction volume so as to prevent the latter from being partly in the substrate and generates other parasite X-rays causing a loss of resolution. For example, the height of the nanostructure is greater than or equal to 500 nm, and less than 1 µm.

Figure 16:
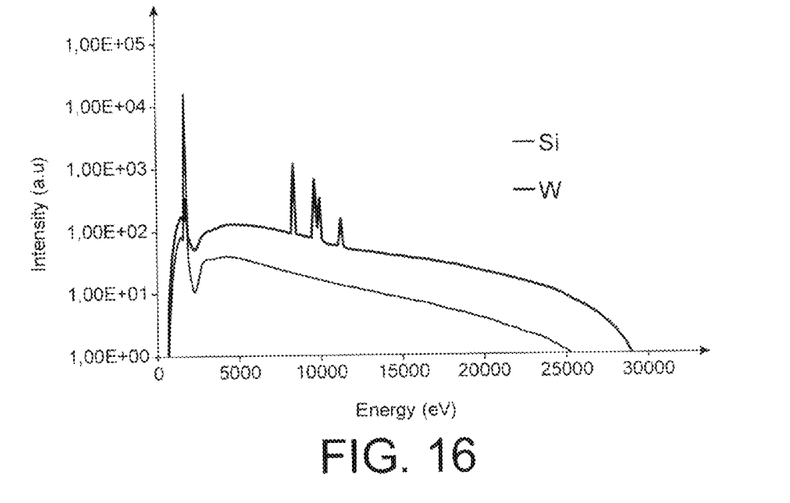
FIG. 16 is a representation of the intensity of the X-rays generated by the silicon and tungsten in function of the energy of the electron beam.

On FIG. 16, the intensities of the X-rays beams generated by silicon and tungsten in function of the energy of the electron beam are shown.

In the case of a nanowire in silicon with a metallic catalyst, the interaction volume reaches the silicon area as it is shown on FIG. 3. But, the spectrum of X-rays that is generated by a material of low atomic number, for example silicon, is very low relative to the spectrum generated by a material of high atomic number, for example the metallic catalyst of a nanowire. On FIG. 16, the intensity of the X-rays generated by silicon is then 10 times lower than the intensity of X-rays generated by tungsten. Therefore, thanks to the invention using a support in a material of low atomic number such as silicon, the support generates few X-rays relative to the metallic catalyst. The specific radiation of silicon, which is represented by the 1700 eV peak, is not detected because the X-ray detectors for imaging usually have a detection window between 3 keV and 10 keV. On the contrary, the typical peak of a metal (peaks around 10 keV for tungsten) are in the detection window of the detectors.

Therefore, thanks to the invention, a target with a support of low atomic number bearing at its free end a material of high atomic number limits the X-rays source to the material with high atomic number. The residual generation of X-rays by the support, for example in silicon, is very low and is not detected.

Advantageously, the nanowire is formed from material having strong thermal conductivity κ to rapidly dissipate heat, such as carbon or silicon. Also, the material of the nanowire is preferably such that it contributes little to generating X-rays to physically limit the interaction volume to the catalyst. These are materials having low atomic numbers, preferably less than 15, and are preferably silicon or carbon.

The catalyst C is also preferably material having strong thermal conductivity for evacuating heat, however it has a higher atomic number, preferably greater than 20, or even greater than 25 for creating high-energy X-rays, at preferred energy levels. By way of advantage, it can be gold or copper. As a variant any metal providing a sufficiently high melting point can be suitable, such as for example iron, cobalt, nickel.

Preferably, the catalyst has a high fusion temperature such that local elevations in temperature do not damage the target or the material of the nanowire. For example, the nanostructure can reach 100° C.

Producing a target by the catalyst and the nanowire is particularly interesting since it employs a known technique for making nanowires. Consequently, fabrication of the target is well controlled, in particular the dimensions of the target are well controlled.

The X-ray beam of nanometric size illuminates the specimen which transmits some of the X-rays which are either detected directly by the detector or previously converted into visible light before being detected.

Using a mobile specimen holder makes it advantageously possible to carry out X-ray tomography to obtain three-dimensional information of the observed object. For this purpose, the specimen can be subjected to rotation before the X-ray nano-sources and X-rays can be recorded at different orientations. This assembly of X-rays serves to reconstruct the internal 3D morphology of the specimen by mathematical processing.

Advantageously, the source of X-rays of nanometric size based on illumination of the catalyst of a nanowire by an electron beam is coupled to tomography and X-ray patterns for improving spatial resolution.

As described hereinabove, the nanostructure can be formed by a nanowire and its catalyst.

According to a variant, the nanostructure is formed by <<batch>> machining. For this, a substrate whereof the material is similar to the material of the nanowire previously described is started with, for example made of silicon or carbon. A thin layer of material, for example gold or copper, similar to the material of the catalyst previously described is deposited onto this substrate. Next, by machining, advantageously by ionic machining (or "Focused Ion Beam" in English terminology), a point is prepared according to the lift-out technique described for example in the document Giannuzzi, L.; Stevie, F.; Giannuzzi, L. A.; Kempshall, B. W.; Schwarz, S. M.; Lomness, J. K.; Prenitzer, B. I.; Stevie, F. A., *FIB Lift-Out Specimen Preparation Techniques. An Introduction to Focused Ion Beams*, Springer US: 2005; pp 201-228]. The point has geometric dimensions similar to the nanowires previously described: for example a cross-section of around 10 nm-100 nm, and a height greater than or equal to 500 nm.

According to another variant, the nanostructure is formed by etching. From a substrate similar to that previously described standard techniques of microelectronics etching can be used. In particular, conventional techniques of reactive ionic etching (RIE for "Reaction Ion Etching" in English terminology) create via interaction between plasma and the substrate nanowires such as described in the document *A Top-down Approach to Fabrication of High-Quality Vertical Heterostructure Nanowire Arrays*, Hua Wang, Minghua Sun, Kang Ding, Martin T. Hill, and Cun-Zheng Ning, Nano Letters 2011 11 (4), 1646-1650. This method for growing nanowires is the so-called top-down method.

Since a small volume of material generates the X-rays, the result is a flow of low-intensity X-rays which produces X-rays with a low signal-to-noise ratio. By way of advantage, a photon-counting detector X can be used such as described in document WO2004064168 to compensate this low ratio. Such a detector is well known to the man skilled in the art and will not be described in detail.

Figure 4:
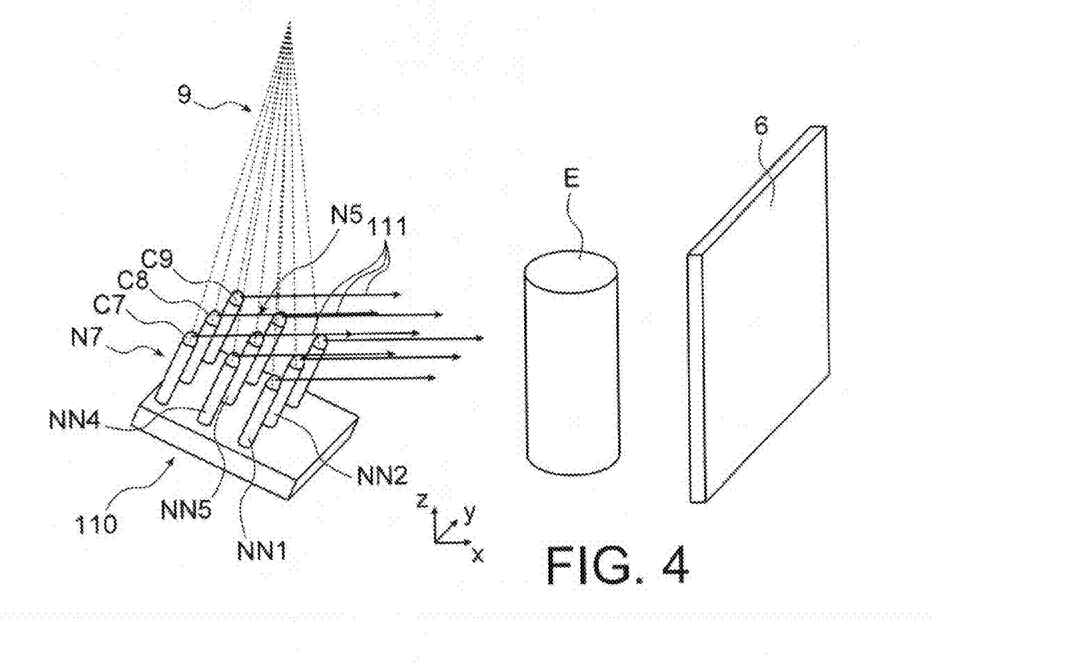
FIG. 4 is a schematic perspective view of another advantageous example of a target which can be used in the source of FIG. 1.

FIG. 4 shows another embodiment of a particularly advantageous target. The target 110 comprises a plurality of juxtaposed nanostructures. In this example, the nanostructures are formed by nanowires NN1, NN2 . . . , NNn surmounted by their catalysts C1, C2 . . . , Cn, n being a positive whole number greater than or equal to 2. As a variant, the nanostructures can be formed by "batch" machining or by etching as described hereinabove.

In the example shown, the nanowires NN1, NN2 . . . , NNn and the catalysts are arranged in a matrix but a random arrangement does not depart from the scope of the present invention. Preferably, the distance between two nanostructures is less than some tens of micrometers, which avoids having excessive differences in enlargement or mismatches on the X-rays, as will be explained hereinbelow.

The target is in fact formed by a plurality of nanostructures, each formed by a catalyst at the apex of a nanowire, each successively emitting an X-ray beam of nanometric size shown schematically by arrows 111 in FIG. 4. The combination of this target with an SEM is particularly advantageous, as will be explained hereinbelow.

Operating such a target is as follows: over a given time the SEM successively illuminates each nanostructure, each successively sending out an X-ray beam of nanometric size, which illuminates the specimen. The latter transmits the X-rays which are detected directly or indirectly by the detector. As will be explained hereinbelow, the data are processed so as to take into account the position of each nanostructure relative to the specimen.

Implementing such a target highly advantageously reduces heating each nanostructure, heating which can be the cause of instabilities and progressive degradation of the target.

In fact, the document Reimer, L., 1998. *Scanning Electron Microscopy, second ed.*, Springer, Berlin, p. 118, describes local heating caused by an electron beam of intensity I accelerated by high voltage $V_0$ in a SEM. This heating is shown as:

$$\Delta T = \frac{1.5}{\pi} \cdot \frac{I.V_0}{\kappa.R}$$

R is the average travel time of electrons in the material and $\kappa$ is the thermal conductivity of the material, corresponding to the material of the catalyst of the nanowire in this case.

Applying this formula to a catalyst made of gold, with I=2 µA and $V_0$=30 kV, results in local heating which can reach 100° C. As mentioned hereinabove, this heating can be responsible for instabilities and progressive degradation of the target generating the X-rays.

Because of using a plurality of nanostructures, it is possible to reduce this heating. In fact, by successively lighting the nanostructures with an exposure time on each nanostructure equal to the overall exposure time divided by the number of nanostructures, the dose of electrons delivered to each nanostructure is decreased.

Each nanostructure generates conical X-ray beams which produce projections on the detector, as is illustrated in FIG. 4. In the example shown, the target comprises nine nanostructures (n=9) forming nine sources of nanometric size, and the dose now deposited is divided by a factor of 9 and the nanostructure lifetime is prolonged by as much.

Because of using a SEM which has standard scanning functionalities by means of the electron beam, it is very easy to scan the different nanostructures.

With the target of FIG. 4, since the nanostructures are successively scanned by the electron beam and the detector integrates all the photons X without distinguishing their emission nanostructure, the overall source of X-rays is the sum of all the contributions coming from each nanostructure, and the overall source then becomes very big. The gain can be limited.

By way of advantage and to eliminate this disadvantage, an image is recorded at each scanning of a nanostructure. This produces X-rays distinct from the specimen from the X-rays sent by each of the nanostructures.

Next, the X-rays are processed to take into account the position of each nanostructure relative to the specimen. In fact, if a system xyz as shown in FIG. 4 is considered, the axis z being oriented towards the specimen and the axes y and z being orthogonal to each other and to the axis x, the nanostructures have different positions in this system relative to the specimen. As is evident in FIG. 4, the matrix of nanostructures is inclined relative to axes x, y and z implying offset in the three directions.

Offset along the axis x causes a difference in enlargement of the specimen since the nanostructures enclosing the central nanostructure N5 are closer to or further away from the specimen than the central nanowire N5.

Six of eight nanostructures enclosing the central nanostructure N5 are also offset along the axis y relative to the central nanostructure N5 and are offset along the axis x relative to the central nanostructure N5.

Since the distribution of the nanostructures on the substrate is known, the X-rays can be processed so as to take this variation in position relative to the specimen into account. The SEM can be programmed to successively scan each nanostructure.

Knowing this distribution, a single image corresponding to a single nanostructure from all the contributions from all the nanostructures can be recalculated digitally to be able to average all the images in the same system and therefore improve the signal-to-noise ratio and retain a source size equal to that of a nanostructure and really acquire a source of X-rays of nanometric size.

Prior to calculation, a series of images is acquired whereof the number corresponds to the number of nanostructures. Geometrically, these images correspond to the same source-specimen-detector orientation but are offset along the three axes x, y and z due to the offsetting of each nanostructure along the three axes x, y and z.

Calculating the single virtual image corresponding to the emission of X-rays originating from a single point is carried out by resampling all the images on common grid, as described hereinbelow. Next comes readjusting of the images formed by the photons X sent by the nanostructures relative to a nanostructure forming the reference nanostructure, which is for example the central nanostructure designated N5 in FIG. 4.

The process of readjusting a radiograph acquired from a nanostructure offset along the axis X and the averaging of this "readjusted" radiograph and of that acquired from a nanostructure forming the reference nanostructure will now be described.

Figure 5:
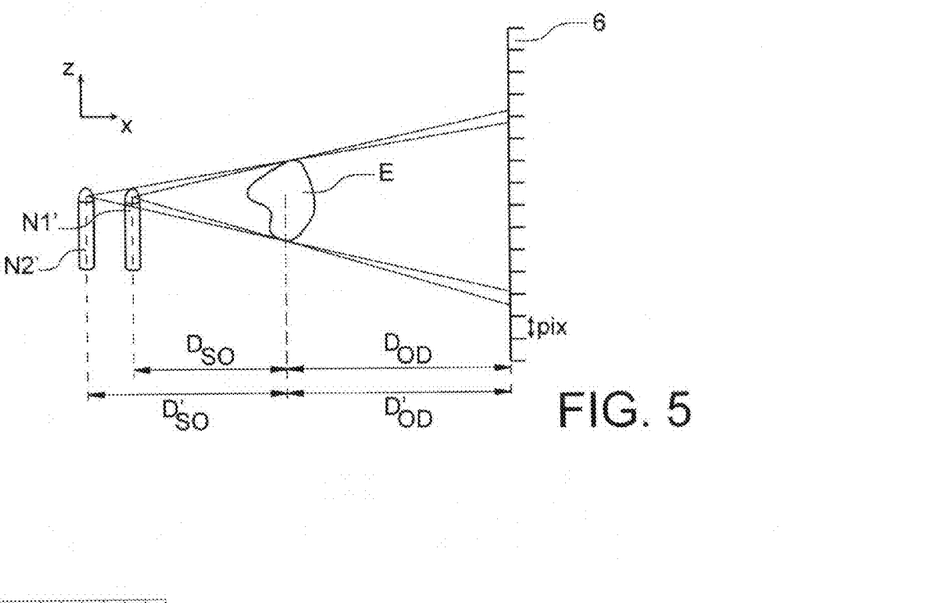
FIG. 5 is a schematic illustration of the disposition of the nanostructures of the target relative to the specimen according to a first direction.

FIG. 5 shows the case of two offset nanostructures N1', N2' along the axis X. In this illustration, there is pure offsetting along the axis x contrary to the illustration of FIG. 4 where the nanostructures at the same time have instances of offsetting along x, y and z.

Images with different enlargements are then obtained. To be able to add up the images formed with X-ray beams generated by two nanostructures having offset positions, it is appropriate to resample the images on the same grid. The nanostructure N1' is considered as the reference nanostructure.

During a first step, the image Image($D_{SO}$) which is formed from X-rays originating from the nanostructure N1' is acquired. The source-object distance is designated $D_{SO}$. Because of the enlargement, the effective pixel size on the image is:

$$\text{Pixel\_réel} = pix \cdot \frac{D_{SO}}{D_{SO} + D_{OD}}$$

$D_{OD}$ is the object-detector distance.

During a following step, the image Image($D'_{SO}$) acquired which is formed from the source formed by the nanostructure N2'. The source-object distance is designated $D'_{SO}$. This image, designated I0, is the least enlarged. The real pixel size is:

$$\text{Pixel\_réel}' = pix \cdot \frac{D'_{SO}}{D'_{SO} + D'_{OD}}$$

During a following step, the image 10 is resampled by approaches well known to the man skilled in the art, for example described in document US 20120082396, on a new grid whereof the pixel is equal to the pixel of the image Image($D_{SO}$). The new image called I1 is illustrated schematically in FIG. 6. This resampling uses for example interpolation, which can be bicubic interpolation. It should be noted that the image Image($D_{50}$) does not need to be readjusted.

Figure 6:
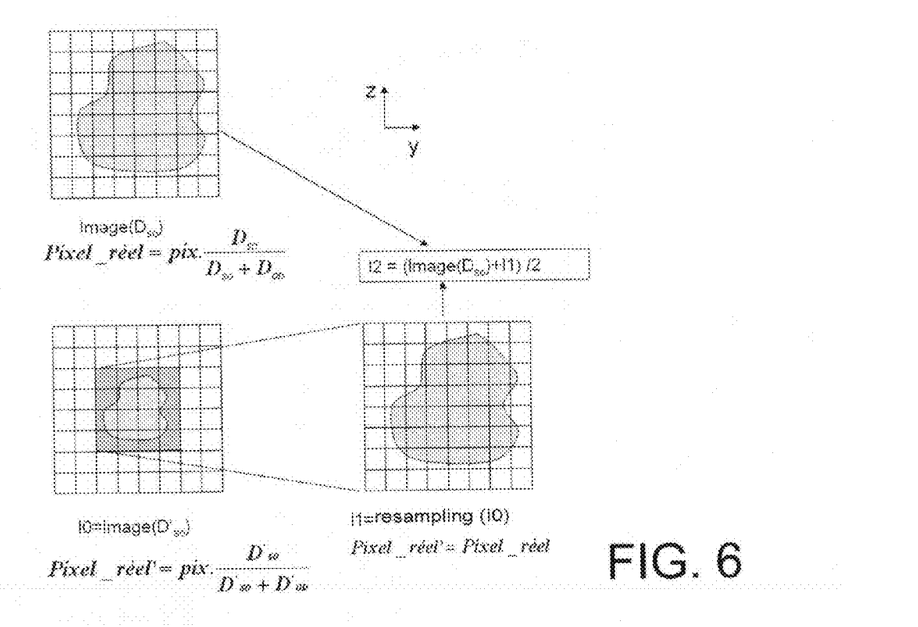
FIG. 6 is a schematic illustration of the averaging of the images obtained by the different nanostructures of FIG. 5 and by preliminary readjusting of the latter.

In a following step, the two images 11 and Image($D_{SO}$) are averaged as is illustrated schematically in FIG. 6, and the resulting image I2 has a better signal-to-noise ratio but retains the resolution corresponding to a single nanowire.

In the case of a multitude of nanowires distributed along the axis X and therefore resulting in formation of a multitude of projections at different enlargements, the steps are repeated for each nanostructure to return all the images to the same enlargement.

Figure 7:
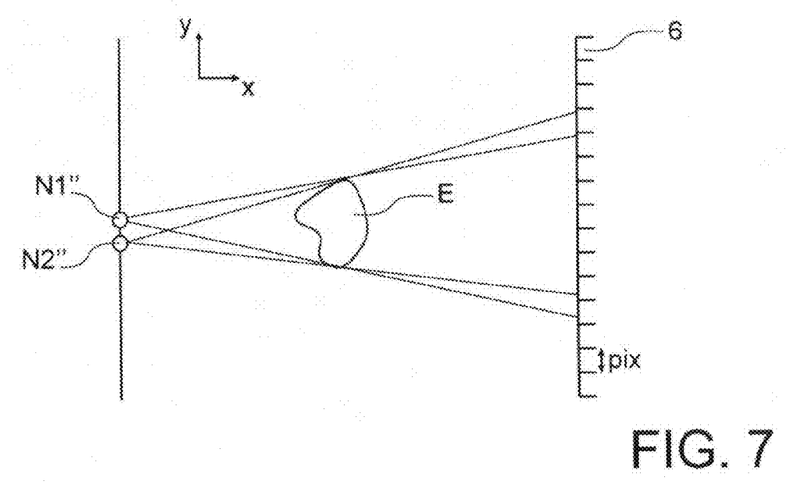
FIG. 7 is a schematic illustration of the disposition of the nanostructures of the target relative to the specimen according to a second direction.

The readjusting process in the case of offsetting of two nanostructures N1", N2" relative to the axis y such as illustrated in FIG. 7 will now be described.

The nanostructures N1", N2" are distributed along the axis y at two different positions according to the axis y. These two nanostructures N1", N2" will produce offset images, as illustrated in FIG. 7.

It is considered that the nanostructure N1" forms the reference nanostructure.

Figure 8:
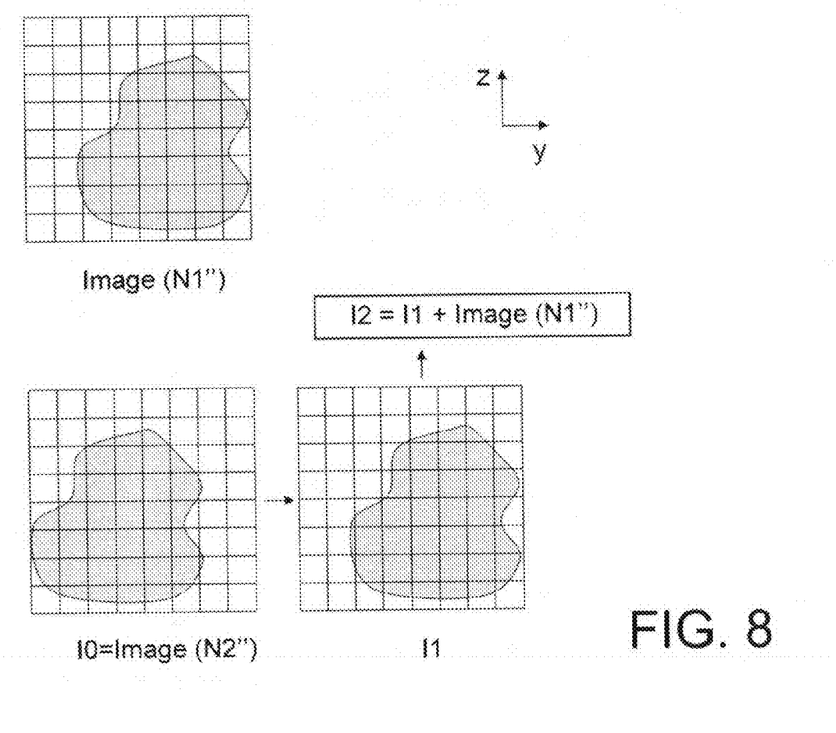
FIG. 8 is a schematic illustration of the averaging of the images obtained by the different nanostructures of FIG. 7 and by preliminary readjusting of the latter.

For the images to be averaged, the images are previously readjusted according to the following steps:
  during a first step the image I of the specimen is acquired from the X-rays generated by the nanostructure N1";
  during a following step the image I0 of the specimen is acquired from the X-rays generated by the nanostructure N2", this nanostructure N2" being offset according to the axis y relative to the nanostructure N1";
  during a following step readjusting of the image I0, relative to the image I acquired with the nanostructure N1" is carried out. This readjusting is achieved by well known methods, such as those described in the document Zitova et al, *Image registration methods: a survey, Image and Vision Computing* 21 (2003) 977-1000. The image is acquired and the image I1 results;
  during following a step the readjusted image I1 is averaged and the image I acquired to obtain the averaged image I2, as is illustrated in FIG. 8.

In the case of a multitude of nanostructures distributed along the axis y and therefore resulting in formation of a multitude of projections all offset to each other, the steps are repeated for each nanostructure to return all the images to the same system.

In the case of offsetting of nanostructures along the axis z, the readjusting process is similar to the readjusting process along the axis y.

In the case of the target with nine nanostructures of FIG. 4, the 9 X-rays are recorded and by processing the 9 X-rays are returned to the same enlargement by resampling and in the same position, those of the X-ray of the central nanostructure.

For this, the steps of the readjusting process are applied successively along the axes x, y and z such as described previously as a function of the positions of the nanostructures.

It will be clear that the choice of reference nanostructure is arbitrary.

A simulation of an example of use of the imaging device according to the invention will not be described.

Figure 9:
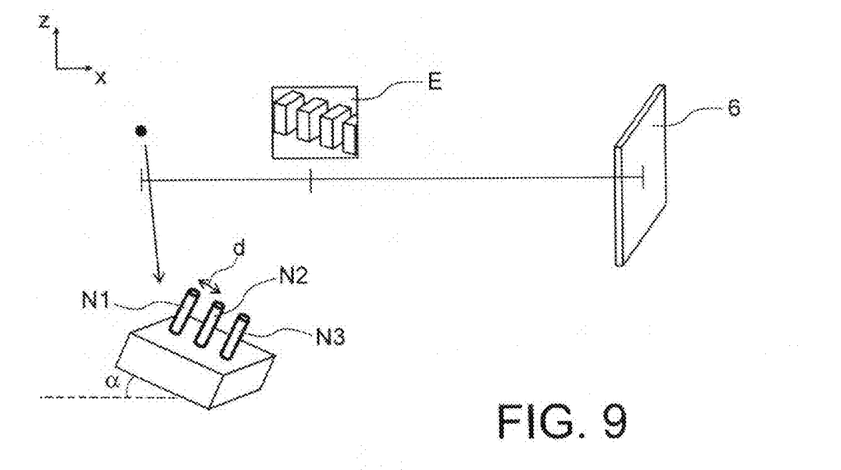
FIG. 9 is a schematic illustration of an example of an imaging device comprising a target with three nanostructures.

FIG. 9 schematically illustrates the device comprising a source of rays having three nanostructures N1, N2, N3, a detector and a specimen E formed by a chart.

The source of X-rays is arranged relative to the axis X such that the three nanostructures are aligned along the axis x and are inclined at an angle α of 45° relative to the axis x. Therefore the nanostructures are offset relative to the axis x and relative to the axis z. The nanostructure N3 is considered as the reference nanostructure.

The X-rays obtained by the three nanostructures therefore have three different enlargements.

If FXn is the distance between the nanostructure Nn and the chart, and d is the distance between two nanostructures, the distances FX1, FX2 and Fx3 are $$FX1 = FX3 + 2d \times \sqrt{2}/2$$

$$FX2 = FX3 + d \times \sqrt{2}/2$$

For example, FX3=300 µm and d=2 µm are chosen and knowing that α=45° was chosen, then $$FX1 = 302.82 \, \mu m$$

$$FX2 = 301.41 \, \mu m$$

$$FX3 = 300 \, \mu m.$$

The angle of inclination α of 45° is advantageous as it has the least shade of one nanowire by another.

Figure 10A:
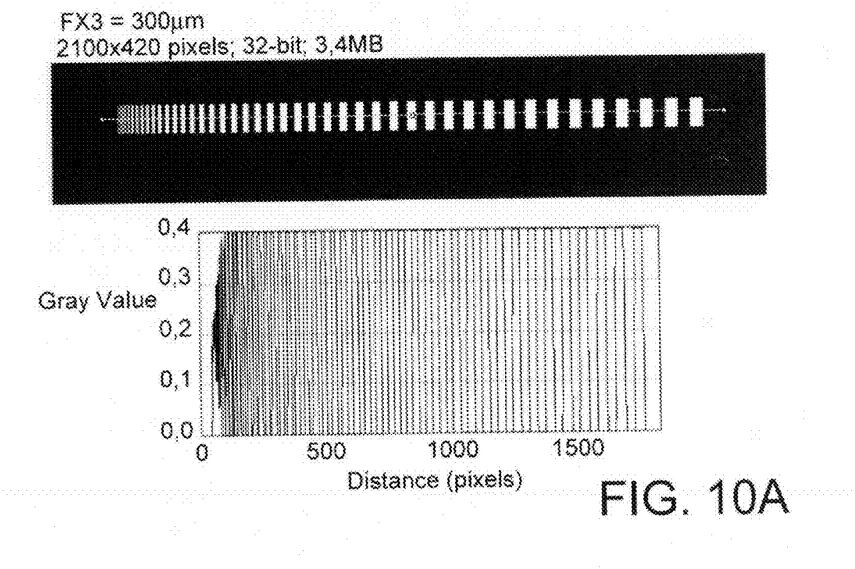
FIGS. 10A to 10C are radiographs of a chart from each of the X-ray beams sent by each of the microstructures of the device of FIG. 9 respectively and their profile of associated greys.
Figure 10B:
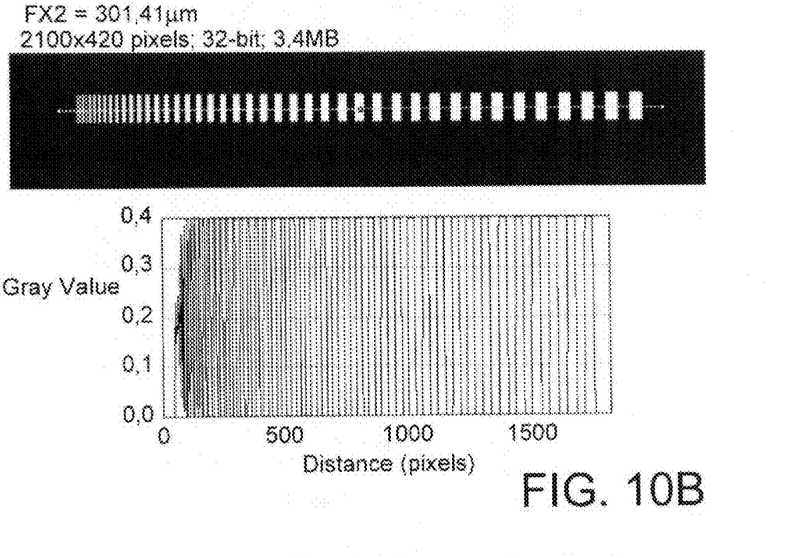
Figure 10C:
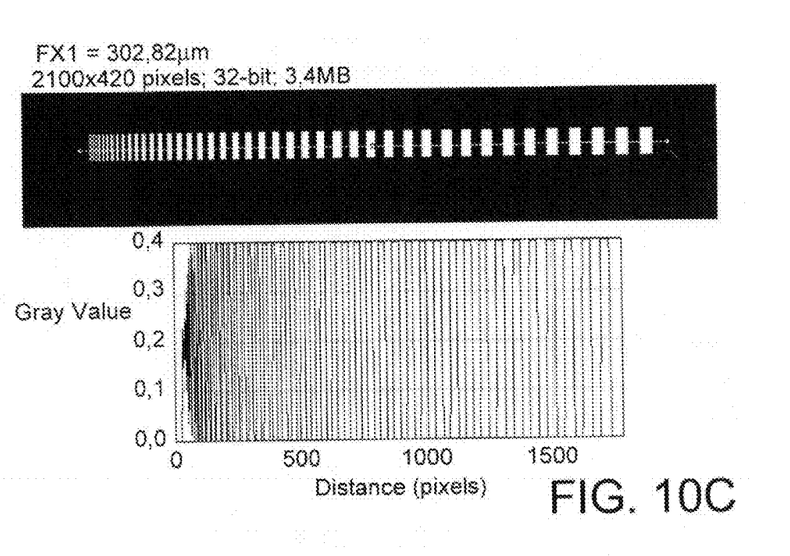

FIGS. 10A, 10B and 10C show respectively the X-ray and the profile of the X-ray obtained from X-rays sent by each nanostructure N1, N2 and N3.

Figure 11:
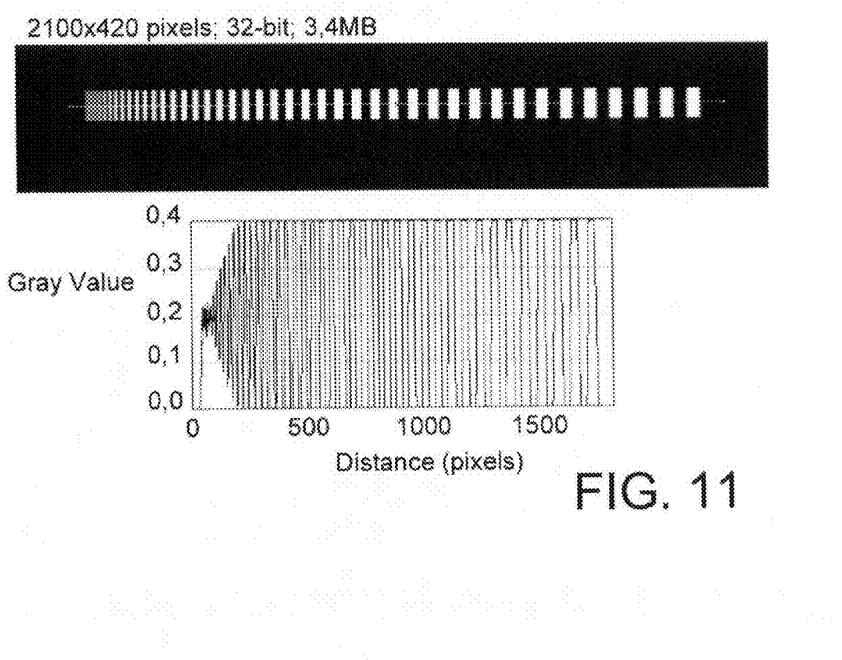
FIG. 11 is a radiograph of the chart obtained by averaging the three X-rays of FIGS. 10A to 10C without readjusting the X-rays and its profile of associated greys.

FIG. 11 shows the X-ray obtained by averaging of the three X-rays of FIGS. 10A, 10B and 10C and the profile of the latter without having readjusted the X-rays of FIGS. 11A and 11B. It is evident that a blurred image is acquired and, on the profile, it is noted by comparison with the other profiles that there is loss of resolution.

The loss of resolution is due to enlargement of the source size, which is the sum of the contributions of the three nanostructures.

As explained hereinabove, the three images are returned to the same enlargement. For this, bicubic interpolation can be employed for example to return the three images to maximum enlargement, as described for example in the document E. H. W. Meijering, "*A chronology of interpolation: From ancient astronomy to modern signal-and image-processing,*" Proc. IEEE, vol. 90, no. 3, pp. 319-342, March 2002.

Figure 12A:
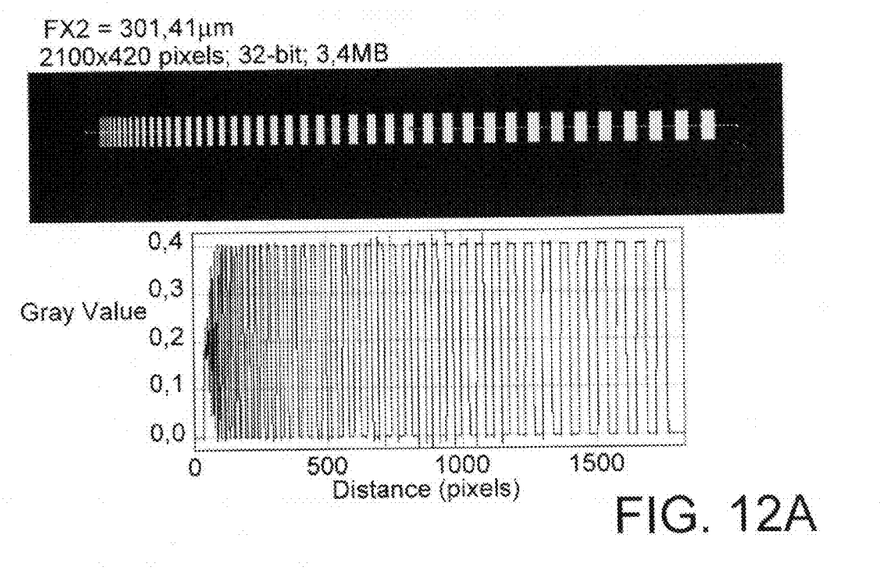
FIGS. 12A and 12B are the radiographs obtained from the radiographs of FIGS. 10B and 10C respectively after cubic interpolation and their profile of associated greys.
Figure 12B:
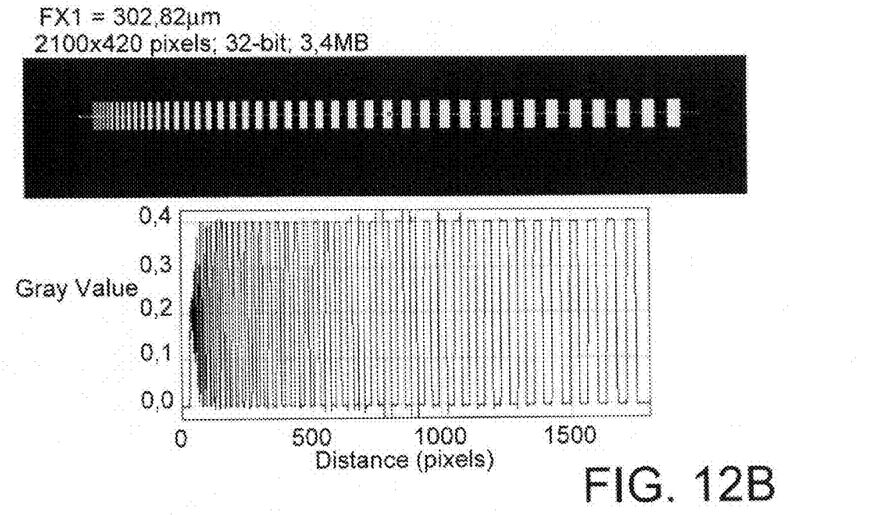

FIGS. 12A and 12B show the images of the nanostructures N2 and N1 after this enlargement, as well as their profile.

The size of the image, that is, the number of pixels which make it up, obtained from the nanostructure N1 is equal to 2110×420 (2110=2100×301,82/300).

The size of the image obtained from the nanostructure N2 is equal to 2120×420 (2110=2100×302, 82/300).

The size of the images is now different from one nanostructure to the other. To sum up, pixels are added. Adding pixels is achieved for example by the so-called <<zero-padding>> method. This method is described for example in the work <<*The Essential Guide to Image Processing*>>, Alan Conrad Bovik, Elsevier, 2009, paragraph 5.4.6, p. 110.

When this method is applied, pixels are added to the image obtained from the nanostructure N1 and that obtained from the nanostructure N3 to attain the number of pixels of the image obtained from the nanostructure N2, that is, 2120×420.

Figure 13A:
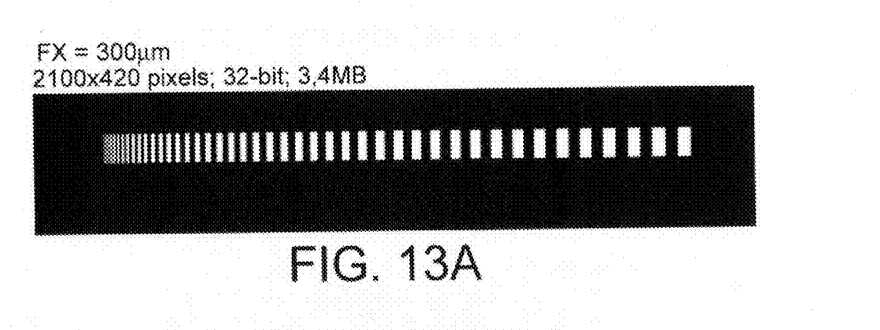
FIGS. 13A and 13B are the radiographs obtained from the radiographs 10A and 12B after a "zero-padding" process respectively and their profile of associated greys.
Figure 13B:
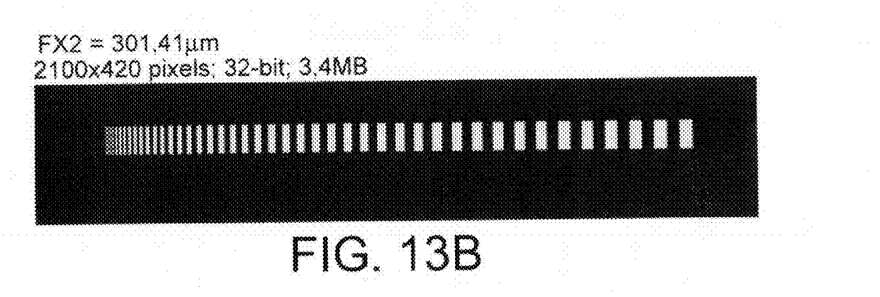

The images resulting from nanostructures N3 and N1 are illustrated in FIGS. 13A and 13B respectively.

Figure 14:
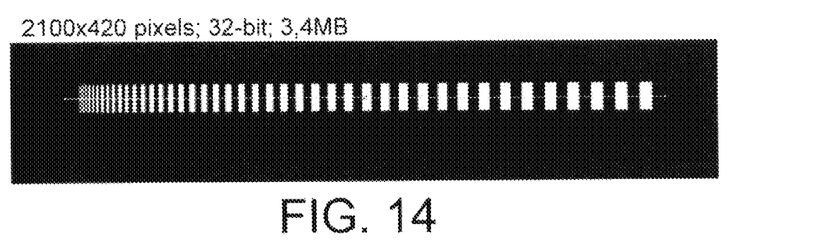
FIG. 14 is the radiograph after averaging of the radiographs of FIGS. 13A, 13B and 12A, and its profile of greys.

The three images can now be added up, giving the image illustrated in FIG. 14.

Figure 15:
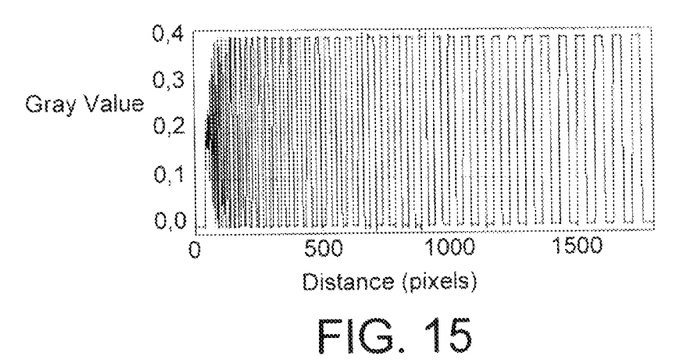
FIG. 15 is the profile of the radiograph of FIG. 14.

FIG. 15 shows the profile of the image of FIG. 14 and, when it is compared to the profile of FIG. 12, a substantial improvement of the resolution is observed because of the processing of images by bicubic interpolation before averaging.

Because of the invention, a source of X-rays of reduced size is obtained for executing imaging of embedded nanostructures with good resolution.

The invention claimed is:

1. A source of X-rays, comprising:
a source of electrons configured to generate an electron beam of nanometric size; and
a target configured to emit an X-ray beam upon illumination by the electron beam, and comprising a plurality of elongated nanostructures each attached at a first end thereof to a substrate and each having a second end disposed at a distance away from a surface of the substrate,
each of the plurality of elongated nanostructures comprising:
a first portion, including the first end attached to the substrate and a body extending from the first end toward the second end, comprising a first material configured to generate low-energy X-rays, and
a second portion covering the second end and comprising a second material configured to generate high-energy X-rays,
wherein the first portion and the second portion have a transverse dimension between 1 nm and 100 nm,
wherein the first portion is offset from neighboring first portions among the plurality of elongated nanostructures in a direction of the transverse dimension, and
wherein the second portion is offset from neighboring second portions among the plurality of elongated nanostructures in the direction of the transverse dimension.

2. The source of X-rays according to claim 1, in which the first material of the first portion has an atomic number less than 15.

3. The source of X-rays according to claim 1, in which the first material of the first portion is silicon or carbon.

4. The source of X-rays according to claim 1, in which the second material of the second portion has an atomic number greater than 20.

5. The source of X-rays according to claim 1, in which the first material and the second material are thermally conductive.

6. The source of X-rays according to claim 1, in which the second material of the second portion is gold or copper.

7. The source of X-rays according to claim 1, in which the offset of the first portions and the offset of the second portions separating two adjacent elongated nanostructures of the plurality of elongated nanostructures is of the order of tens of nanometers.

8. The source of X-rays according to claim 1, in which the source of electrons is a scanning electron microscope.

9. The source of X-rays according to claim 7, in which the source of electrons is a scanning electron microscope and in which a disposition of the plurality of elongated nanostructures is registered in a scanning control of the scanning electron microscope such that the electron beam emitted by the scanning electron microscope is configured to successively illuminate all of the plurality of elongated nanostructures.

10. The source of X-rays according to claim 1, in which a height of each of the plurality of elongated nanostructures is greater than or equal to 500 nm.

11. The source of X-rays according to claim 1, in which the first portion comprises a nanowire and the second portion comprises a catalyst covering an end of the nanowire.

12. The source of X-rays according to claim 1, in which the plurality of elongated nanostructures comprise an etched substrate material comprising the second material of the second portion covered by a layer of the first material of the first portion.

13. The source of X-rays according to claim 1, in which the plurality of elongated nanostructures comprise a machined substrate material comprising the second material of the second portion covered by a layer of the first material of the first portion.

14. An X-ray imaging device, comprising:
- at least one source of X-rays according to claim 1;
- a specimen holder configured to hold a specimen; and
- at least one direct or indirect detector of X-rays transmitted by the specimen.

15. The X-ray imaging device according to claim 14, in which the specimen holder is configured to be rotatably mobile so as to allow imagery by tomography.

16. The X-ray imaging device according to claim 14, in which the at least one direct or indirect detector is a photon-counting detector.

17. An imaging process of a specimen comprising at least one microstructure and/or at least one nanostructure using an X-ray imaging device comprising at least one source of X-rays, a specimen holder configured to hold the specimen, and at least one direct or indirect detector of X-rays transmitted by the specimen,
said source of X-rays comprising;
- a source of electrons configured to generate an electron beam of nanometric size, and
- a target configured to emit an X-ray beam upon illumination by the electron beam, and comprising a plurality of elongated nanostructures each attached at a first end thereof to a substrate and each having a second end disposed at a distance away from a surface of the substrate, each of the plurality of elongated nanostructures comprising:
- a first portion, including the first end attached to the substrate and a body extending from the first end toward the second end, comprising a first material configured to generate low-energy X-rays, and
- a second portion covering the second end and comprising a second material configured to generate high-energy X-rays,
wherein the first portion and the second portion have a transverse dimension between 1 nm and 100 nm,
wherein the first portion is offset from neighboring first portions among the plurality of elongated nanostructures in a direction of the transverse dimension, and
wherein the second portion is offset from neighboring second portions among the plurality of elongated nanostructures in the direction of the transverse dimension,
said imaging process comprising:
- illuminating the plurality of elongated nanostructures by the electron beam; and
- collecting, by the detector, X-rays transmitted by the specimen to obtain at least one X-ray image of the specimen.

18. The imaging process according to claim 17,
wherein the offset of the first portions and the offset of the second portions, each separating two adjacent elongated nanostructures of the plurality of elongated nanostructures, are of the order of tens of nanometers,
wherein the source of electrons is a scanning electron microscope, and
wherein the illuminating and the collecting are performed successively on said each of the elongated nanostructures,
the process further comprising:
- processing the obtained at least one X-ray image to produce at least one modified X-ray image in which the collected X-rays have a same enlargement and/or to produce at least one readjusted X-ray image relative to a reference X-ray image; and
- averaging of the at least one modified X-ray image and/or the at least one readjusted X-ray image.

19. The source of X-rays according to claim 12, in which the plurality of elongated nanostructures comprise a reactive ionic etched substrate material comprising the second material of the second portion covered by a layer of the first material of the first portion.

20. The source of X-rays according to claim 13, in which the plurality of elongated nanostructures comprise an ionic machined substrate material comprising the second material of the second portion covered by a layer of the first material of the first portion.

* * * * *